(12) United States Patent
Farley et al.

(10) Patent No.: US 10,729,461 B2
(45) Date of Patent: Aug. 4, 2020

(54) ILLUMINATED INFUSION CANNULA

(71) Applicant: Novartis AG, Basel (CH)

(72) Inventors: Mark Harrison Farley, Laguna Hills, CA (US); Alireza Mirsepassi, Irvine, CA (US); Michael J. Papac, North Tustin, CA (US)

(73) Assignee: Alcon Inc., Fribourg (CH)

( * ) Notice: Subject to any disclaimer, the term of this patent is extended or adjusted under 35 U.S.C. 154(b) by 76 days.

(21) Appl. No.: 15/974,818

(22) Filed: May 9, 2018

(65) Prior Publication Data

US 2018/0338776 A1 Nov. 29, 2018

Related U.S. Application Data

(60) Provisional application No. 62/510,362, filed on May 24, 2017.

(51) Int. Cl.
| | |
|---|---|
| *A61B 17/34* | (2006.01) |
| *A61F 9/007* | (2006.01) |
| *A61B 90/30* | (2016.01) |
| *A61B 1/07* | (2006.01) |

(52) U.S. Cl.
CPC .......... *A61B 17/3421* (2013.01); *A61B 90/30* (2016.02); *A61F 9/00736* (2013.01); *A61F 9/00781* (2013.01); *A61B 1/07* (2013.01); *A61B 2090/306* (2016.02)

(58) Field of Classification Search
CPC . A61B 17/3421; A61B 1/07; A61B 2090/306; A61B 90/30; A61B 1/00; A61B 1/06; A61B 1/00112; A61B 1/313; A61B 1/00117; A61B 17/3478; A61F 9/00781; A61F 9/00736; A61F 9/007; A61F 9/00; A61F 9/0008; A61M 2025/0042; A61M 25/00; A61M 25/0023; A61M 25/0026; A61M 25/0021
See application file for complete search history.

(56) References Cited

U.S. PATENT DOCUMENTS

| | | | |
|---|---|---|---|
| 3,990,453 | A | 11/1976 | Douvas |
| 4,168,707 | A | 9/1979 | Douvas et al. |
| 4,200,106 | A | 4/1980 | Dinkelkamp |
| 5,201,730 | A | 4/1993 | Easley |
| 5,275,593 | A | 1/1994 | Easley et al. |
| 5,425,730 | A | 6/1995 | Luloh |

(Continued)

FOREIGN PATENT DOCUMENTS

| | | |
|---|---|---|
| GB | 1349881 | 4/1974 |
| WO | WO2007133267 A1 | 11/2007 |

(Continued)

OTHER PUBLICATIONS

Alcon Global Vitreoretinal Product Catalog, pp. 25-40, dated 2014.

*Primary Examiner* — Jason E Flick

(57) ABSTRACT

A method and system provide a surgical infusion device including a cannula and an optical fiber coupled with the cannula. The cannula has a channel therethrough and an outside diameter. The channel has an inside diameter that is smaller than the outside diameter. The optical fiber is coupled with the cannula. At least a portion of the optical fiber coupled with the cannula has a diameter of not more than one half the inside diameter.

13 Claims, 7 Drawing Sheets

(56) References Cited

U.S. PATENT DOCUMENTS

| | | | |
|---|---|---|---|
| 5,591,160 A | 1/1997 | Reynard | |
| 5,632,740 A * | 5/1997 | Koch | A61B 3/0008 |
| | | | 362/554 |
| 5,651,783 A | 7/1997 | Raynard | |
| 6,939,341 B2 | 9/2005 | Vijfvinkel | |
| 7,783,346 B2 | 8/2010 | Smith et al. | |
| 8,292,434 B2 | 10/2012 | Horvath et al. | |
| 8,900,139 B2 | 12/2014 | Yadlowsky | |
| 8,968,347 B2 | 3/2015 | McCollam | |
| 8,979,867 B2 | 3/2015 | Peyman | |
| 9,055,885 B2 | 6/2015 | Horvath | |
| 9,089,364 B2 | 7/2015 | Bhadri | |
| 9,364,982 B2 | 6/2016 | Schaller | |
| 9,402,643 B2 | 8/2016 | Auld | |
| 9,561,085 B2 | 2/2017 | Yadlowsky | |
| 9,839,749 B2 | 12/2017 | Johnson | |
| 9,956,053 B2 | 5/2018 | Diao | |
| 10,016,248 B2 | 7/2018 | Mirsepassi | |
| 10,039,669 B2 | 8/2018 | Heeren | |
| 10,244,931 B2 | 4/2019 | Kern | |
| 10,278,785 B2 | 5/2019 | Mirsepassi | |
| 10,295,718 B2 | 5/2019 | Mirsepassi | |
| 10,376,414 B2 | 8/2019 | Hallen | |
| 2005/0171507 A1 * | 8/2005 | Christian | A61F 9/007 |
| | | | 604/524 |
| 2008/0058704 A1 | 3/2008 | Hee | |
| 2009/0161384 A1 | 6/2009 | Smith | |
| 2009/0182313 A1 | 7/2009 | Auld | |
| 2010/0173866 A1 * | 7/2010 | Hee | A61F 9/0017 |
| | | | 514/54 |
| 2011/0282160 A1 | 11/2011 | Bhadd | |
| 2013/0079598 A1 | 3/2013 | Auld et al. | |
| 2013/0172677 A1 * | 7/2013 | Kennedy, II | A61B 1/051 |
| | | | 600/112 |
| 2014/0121469 A1 | 5/2014 | Meckel | |
| 2014/0210116 A1 | 7/2014 | Schaller | |
| 2014/0357957 A1 | 12/2014 | Bhadri | |
| 2015/0011839 A1 | 1/2015 | Auld | |
| 2016/0113722 A1 | 4/2016 | Heeren | |
| 2016/0228207 A1 | 8/2016 | Yadlowsky | |
| 2016/0302878 A1 | 10/2016 | Kern | |
| 2017/0014023 A1 | 1/2017 | Kern | |
| 2017/0014267 A1 | 1/2017 | Kern | |
| 2017/0119491 A1 | 5/2017 | Mirsepassi | |
| 2017/0165114 A1 | 6/2017 | Hallen | |
| 2017/0172694 A1 | 6/2017 | Dos Santos | |
| 2017/0176660 A1 | 6/2017 | Mirsepassi | |
| 2017/0252121 A1 | 9/2017 | Diao | |
| 2018/0055596 A1 | 3/2018 | Johnson | |
| 2018/0132963 A1 | 5/2018 | Diao | |
| 2018/0133057 A1 | 5/2018 | Diao | |
| 2018/0168768 A1 | 6/2018 | Mirsepassi | |
| 2018/0168861 A1 | 6/2018 | Mirsepassi | |
| 2018/0338776 A1 | 11/2018 | Farley | |
| 2018/0338859 A1 | 11/2018 | Mirsepassi | |
| 2018/0338860 A1 | 11/2018 | Farley | |

FOREIGN PATENT DOCUMENTS

| | | |
|---|---|---|
| WO | WO2016154186 A1 | 9/2016 |
| WO | WO2017009723 A1 | 1/2017 |
| WO | WO2017072613 A1 | 5/2017 |

* cited by examiner

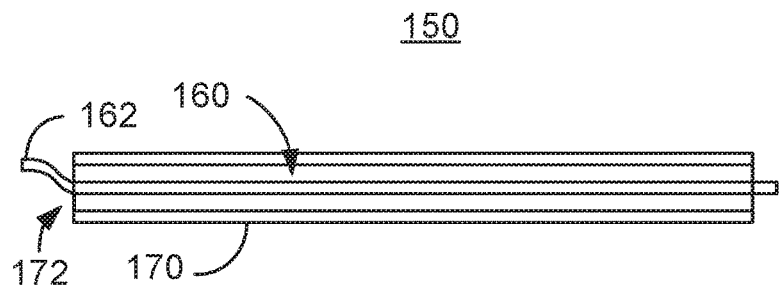
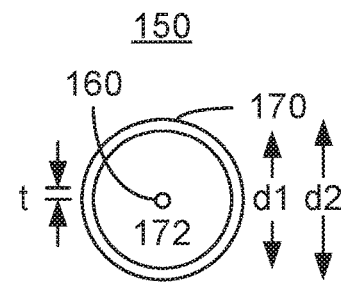
FIG. 4A  FIG. 4B
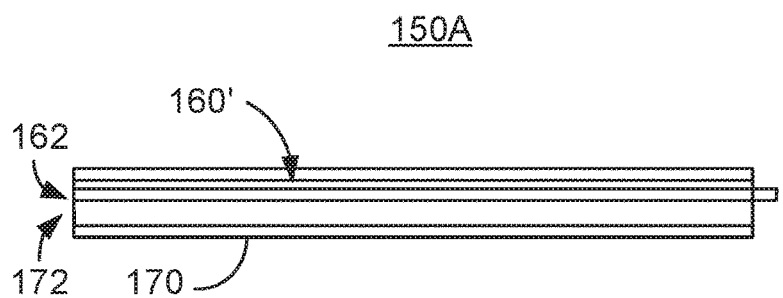
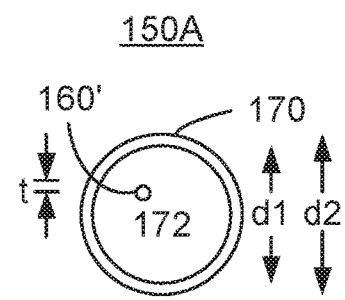
FIG. 5A  FIG. 5B
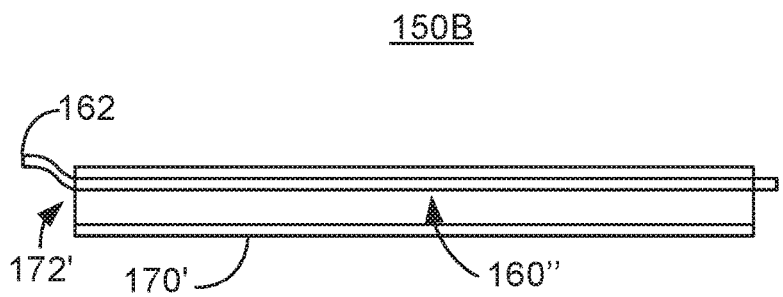
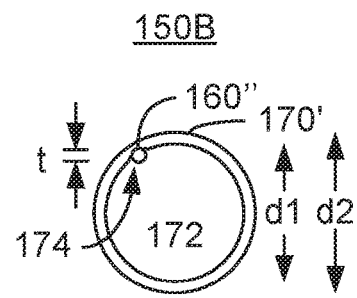
FIG. 6A  FIG. 6B

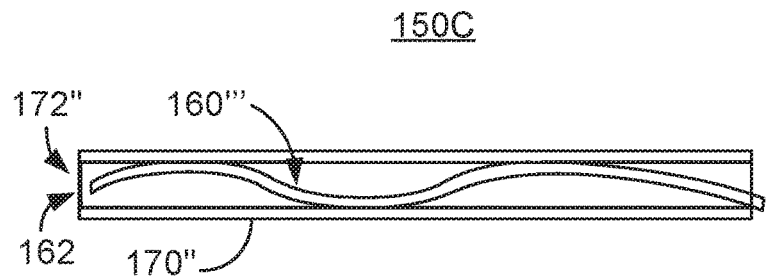
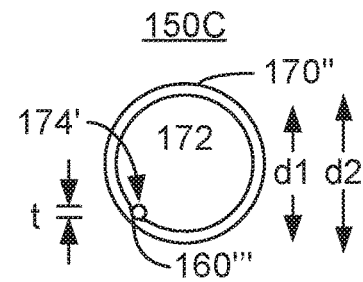
FIG. 7A
FIG. 7B
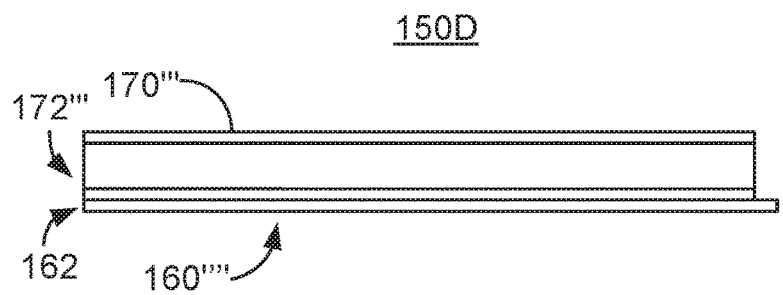
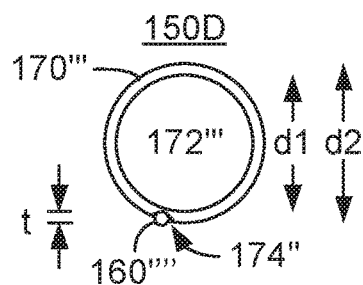
FIG. 8A
FIG. 8B
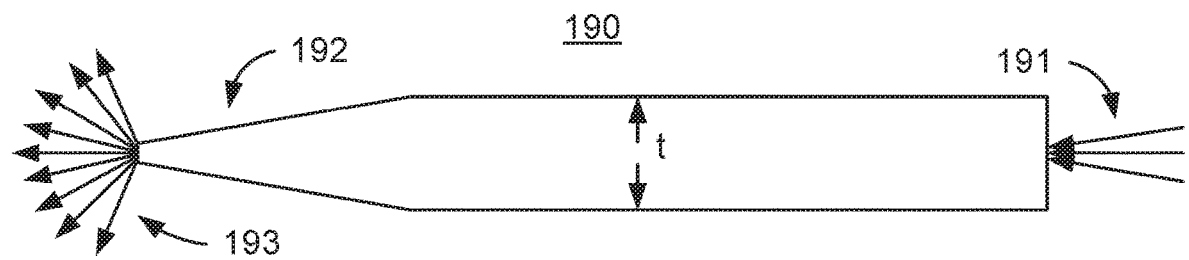
FIG. 9
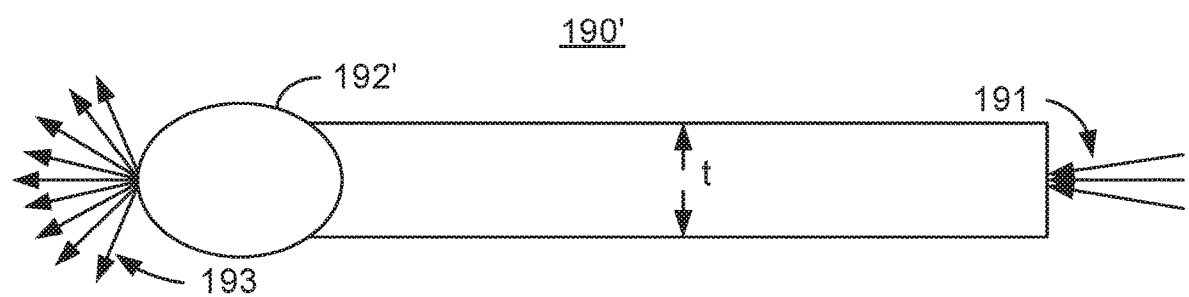
FIG. 10

ILLUMINATED INFUSION CANNULA

This application claims the benefit of priority of U.S. Provisional Patent Application Ser. No. 62/510,362 titled "Illuminated Infusion Cannula", filed on May 24, 2017, whose inventors are Mark Harrison Farley, Alireza Mirsepassi, and Michael J. Papac, which is hereby incorporated by reference in its entirety as though fully and completely set forth herein.

BACKGROUND

Ophthalmic surgery for the back of the eye (e.g. in the vitreous humor) frequently involves multiple ports, or apertures, into the eye through which various instruments are inserted. For example, in bimanual surgery, four ports are used and four incisions through the sclera may be made. One port is used for the infusion cannula, through which a balanced salt solution (BSS) is injected into the eye. The infusion of fluid aids in maintaining the internal eye pressure during surgery. An illumination cannula is inserted through the second port. The illumination cannula carries a conventional optical fiber therein. The conventional optical fiber is typically formed of plastic and has a diameter on the order of 400-500 micrometers. This size is very close to the inside diameter of the illumination cannula. The conventional optical fiber provides illumination for the surgical field. In some embodiments, the optical fiber is fixed to the patient's head so that the surgical field can be lighted without occupying the surgeon's hand. The third port is used for a vitrectomy probe or other surgical instrument. The fourth port may be used for forceps, scissors or another tool which the surgeon uses in the procedure.

Although the ophthalmic surgery may be performed, there are possible negative outcomes that increase with the number of ports used. Using four ports requires the surgeon to make four incisions in the sclera and to monitor surgical instruments at four different locations. This makes the procedure more difficult for the surgeon. A higher number of ports also carries a higher risk of complications and other negative outcomes for the patient than fewer ports. Additional ports, which are sometimes used for other purposes, may also make surgery more difficult for the physician and increase the risks for the patient.

Accordingly, what is needed is a mechanism for assisting a physician in ophthalmic surgery which decreases the number of required surgical incisions and access ports, which may thereby provide the possibility of improved ease of surgery, reduced surgical complications, and improved patient outcomes.

BRIEF SUMMARY

A method and system provide a surgical infusion device including a cannula and an optical fiber. The cannula has a channel therethrough and an outside diameter. The channel has an inside diameter that is smaller than the outside diameter. The optical fiber is coupled with the cannula. A least a portion of the optical fiber coupled with the cannula has a diameter of not more than one half the inside diameter. In some embodiments, this diameter may not be more than one hundred micrometers. Consequently, the surgical infusion device may be used both for infusion and for illumination, thereby forming an illuminated infusion cannula. In some embodiments, the optical fiber may be centrally mounted in the cannula (e.g., extending close to the center of the cannula). In some embodiments, the optical fiber may be mounted off-center or even along a side of the cannula.

According to the method and system disclosed herein a single instrument may provide both illumination and infusion, allowing for fewer ports and the possibility of improved patient outcomes.

BRIEF DESCRIPTION OF SEVERAL VIEWS OF THE DRAWINGS

FIGS. 4A and 4B are side and end views of another exemplary embodiment of an illuminated infusion cannula.

FIGS. 5A and 5B are side and end views of another exemplary embodiment of an illuminated infusion cannula.

FIGS. 6A and 6B are side and end views of another exemplary embodiment of an illuminated infusion cannula.

FIGS. 7A and 7B are side and end views of another exemplary embodiment of an illuminated infusion cannula.

FIGS. 8A and 8B are side and end views of another exemplary embodiment of an illuminated infusion cannula.

FIG. 9 depicts an exemplary embodiment of an optical fiber usable in an illuminated infusion cannula.

FIG. 10 depicts another exemplary embodiment of an optical fiber usable in an illuminated infusion cannula.

DETAILED DESCRIPTION

The exemplary embodiments relate to surgical instruments, such as those used in ophthalmic surgery. The following description is presented to enable one of ordinary skill in the art to make and use the various embodiments that are provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the disclosure. The exemplary embodiments will also be described in the context of particular methods having certain elements. However, the method and system operate effectively for other methods having different and/or additional elements and elements in different orders that are not inconsistent with the exemplary embodiments. Thus, the present disclosure is not intended to be limited to the embodiments shown, but is to be accorded the widest scope consistent with the principles and features described herein.

The method and system are also described in terms of singular items rather than plural items. For example, an optical fiber is used and/or shown in some embodiments. One of ordinary skill in the art will recognize that these singular terms encompass plural. For example, multiple optical fibers might be used.

A method and system provide a surgical infusion device including a cannula and an optical fiber coupled with the cannula. The cannula has a channel therethrough and an outside diameter. The channel has an inside diameter that is smaller than the outside diameter. The optical fiber is coupled with the cannula. At least a portion of the optical fiber coupled with the cannula has a diameter of not more than one half the inside diameter. In some embodiments, this diameter of the optical fiber may not be more than one hundred micrometers. Consequently, the surgical infusion device may be used both for infusion and for illumination. The surgical infusion device may thus be an illuminated infusion cannula.

Figure 1A:
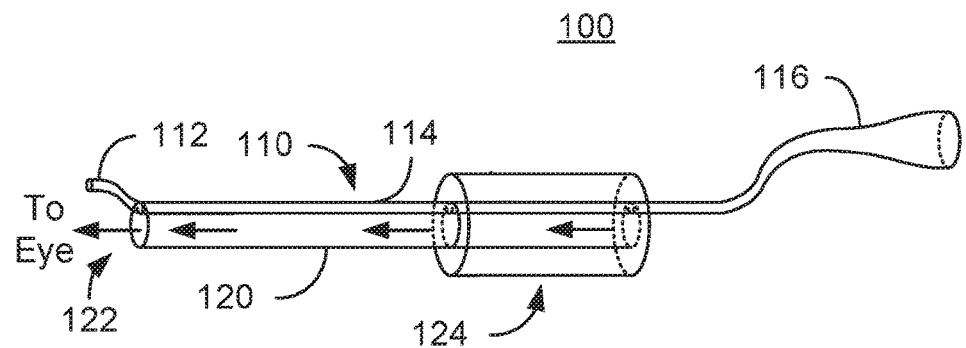
FIGS. 1A and 1B are diagrams depicting an exemplary embodiment of a surgical infusion device and the surgical infusion device used in conjunction with a console.
Figure 1B:
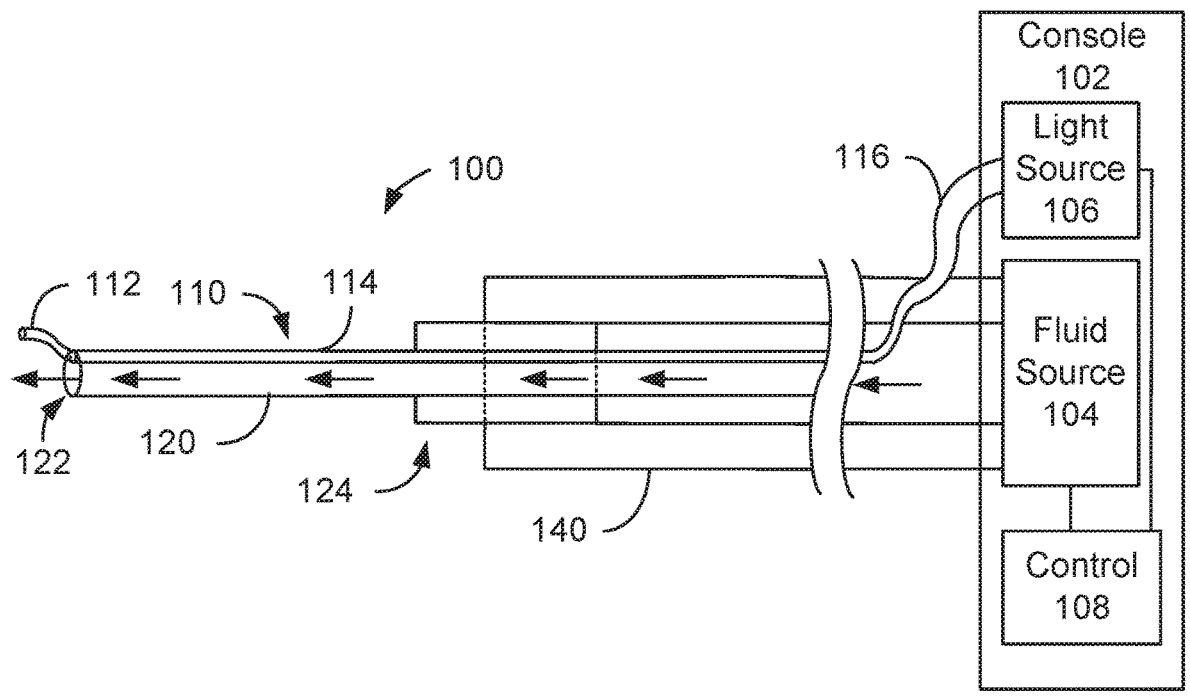

FIGS. 1A and 1B are diagrams depicting an exemplary embodiment of a surgical infusion device 100 usable in ophthalmic surgery and the surgical infusion device 100 when used in conjunction with a console 102. As discussed below, the surgical infusion device provides both illumination and infusion. Consequently, such a surgical infusion device may also be termed an illuminated infusion cannula. FIGS. 1A and 1B are not to scale and for explanatory purposes only. Thus, a particular illuminated infusion cannula is not intended to be shown.

The illuminated infusion cannula 100 includes an optical fiber 110 and a cannula 120. Also shown in FIG. 1B is an infusion line 140 that may be coupled with the cannula 120. Although described as an infusion line 140, the infusion line 140 may also be known as an irrigation line. The infusion line 140 may be formed of plastic tubing and carries fluid to the channel 122. Other materials for the infusion line 140 are also possible.

The cannula 120 is hollow, having a channel 122 therein. In the embodiment shown, the channel 122 is along the axis of the cannula 120. Therefore, although not explicitly indicated in FIGS. 1A-1B, the cannula has an inside diameter that is the diameter of the channel 122 and an outside diameter. The inside diameter is less than the outside diameter by at least the thickness of the walls of the cannula 120. The cannula 120 may be a 23, 25 or 27 gauge cannula in some embodiments. A fluid such as a BSS® (Balanced Salt Solution) irrigating solution may flow from the infusion line 140, through the channel 122 and into the eye. This flow of fluid is indicated in FIGS. 1A-1B by arrows passing through the channel 122. Consequently, the fluid flow through the cannula 120 may be used to maintain the eye pressure during a procedure.

The optical fiber 110 is coupled with the cannula 120. In the embodiment shown, at least part of the optical fiber is within the channel 122. Also in the embodiment shown, the optical fiber 110 lies along the wall of channel 122. In other embodiments, the optical fiber 110 may be at another location. For example, the optical fiber may be along the axis of the cannula 110 or in another position in the channel 122. Alternatively, the optical fiber 122 may be along the outside of the cannula 120. The optical fiber 110 is also shown as being parallel to the axis of the channel 122. In other embodiment, the optical fiber 110 may be curved or retained within or around the cannula 120 in another manner.

The diameter of at least a portion of the optical fiber 110 is small in comparison to the diameter of the channel 122. In some embodiments, the portion of the optical fiber 110 within the channel 122 has a diameter that may not be more than one-half the inside diameter of the channel 122. In some embodiments, the diameter of the optical fiber 110 may not be more than one hundred micrometers. In some such embodiments, at least the portion of the optical fiber 110 within the channel 122 has a diameter of not more than sixty micrometers. This diameter of the optical fiber 110 may be not more than fifty micrometers in some cases. For example, at least the portion of the optical fiber 110 within the channel may have a diameter of less than fifty micrometers and at least thirty micrometers. Some or all of the optical fiber 110 may have such a small diameter even if the optical fiber 110 lies along the cannula 110, outside of the channel 122.

In some embodiments, the optical fiber 110 is a fused silica (e.g. glass) fiber or a borosilicate fiber. In other embodiments, only the portion of the optical fiber 110 having the reduced diameter discussed above is formed of fused silica and/or borosilicate. Plastic may not be used for the reduced diameter portion of the optical fiber 110, such as portions 112 and 114. This allows the optical fiber 110 to withstand the heat generated by light transmitted through the optical fiber 110. However, in other embodiments, additional or different material(s) may be used.

The optical fiber 110 may be formed by heating and drawing a fiber that initially has a larger diameter. Such a fiber may also be tapered. One such embodiment is shown in FIGS. 1A-1B. The optical fiber 110 has portions 112 and 114 having the diameter described above. Another portion 116 may have a larger diameter and is connected to the console 102. Thus, portions 112 and 114 may be formed by drawing an optical fiber having a diameter at least as large as that of the portion 116. Such a fiber may be heated using a laser and pulled to provide an optical fiber at least part of which has the smaller diameter described above. In other embodiments, the optical fiber consists of small diameter portions 112 and 114, but is coupled with another fiber 116 that may have a larger diameter at the proximal input end, and that may be tapered to a smaller diameter where it is coupled to optical fiber 110. Portion 112 of the optical fiber 110 extends out of the channel 122 of the cannula 120. Thus, the tip of the optical fiber 110 is outside of the channel 122. However, in other embodiments, the optical fiber 110 terminates at the tip/end of or within the channel 122 of the cannula 120.

In the embodiment shown in FIGS. 1A-1B, the tip of the optical fiber 110 may be flat cleaved. In other embodiments, the tip of the optical fiber 110 may be configured in another manner. For example, the tip of the optical fiber 110 may be tapered, have a scattering tip or otherwise shaped to provide the desired illumination. Because it has a small diameter and may not be unduly lossy, the optical fiber 110 may concentrate the light input to the end 11. This may not only increase the temperature of the optical fiber 110, but also the intensity of the light output by the optical fiber 110. However, the more intense light illuminates a smaller area. Consequently, a tapered or scattering tip which directly light in multiple directions may be desired to increase the field that is illuminated. If the flat cleaved tip shown is used, then the input launch angle of the beam into the optical fiber 110 may be increased in order to augment scattering. For example, the input launch half-angle may be at least thirty degrees from the axis of the fiber 116. Thus, a high numerical aperture may also be desired for the optical fiber 110. Alternatively, the tip of the optical fiber 110 may be shaped or have another component used to increase the size of the area illuminated.

The illuminated infusion cannula 100 is shown in use in FIG. 1B. The illuminated infusion cannula 100 is coupled with the console 102. The console 102 includes a fluid source 104, control block 108 and light source 106. In other embodiments, the fluid source 104 and/or light source 106 may be physically separated from the console. The control block 108 may include a processor executing instructions stored in a memory and capable of communicating an input/output device such as a graphical user interface (GUI) or other mechanism that the user employs to control the fluid flow and light. The fluid source 104 is coupled with the cannula 120 via the infusion line 140, which may be formed of tubing. The fluid source 104 may be a source of BSS®. The BSS® in the fluid source 104 can be placed under a positive pressure and driven through the infusion line 140. The light source 106 is coupled with the small-diameter portions 112 and 114 of the optical fiber via portion 116. As discussed above, some or all of the portion 116 may be formed of a different optical fiber coupled to the optical fiber 110. A user, such as a surgeon, may control the illumination, fluid, and/or other electronics for the illuminated infusion cannula 100 using the console 102.

In operation, the cannula 120 may be inserted into an incision in the eye to perform ophthalmic surgery. In some embodiments, the cannula 110 may be inserted into another cannula, such as a trocar cannula already being used in the procedure. The surgeon may make additional incision(s) for other purposes. Fluid may flow from the fluid source 104 through infusion line 140 and through the channel 122 of the cannula 120. The arrows within the infusion line 140 and cannula 120 depict the direction of fluid flow. Because the diameter of the optical fiber 110 is significantly smaller than the diameter of the channel 122, the optical fiber occupies a very small portion of the cross section of the channel 122. This allows the fluid to flow relatively freely through the cannula 120. Consequently, eye pressure may be maintained.

In addition, light from the light source 106 is coupled into the optical fiber 110. As discussed above, the light may be scattered from the tip of the optical fiber 110 in order to illuminate a larger region. As a result, the illuminated infusion cannula may not only illuminate the operating field, but also provide fluid to the eye.

The illuminated infusion cannula 100 may result in improved outcomes. Because both illumination and fluid are provided via a single device 100, only one incision may be made in the eye to provide light and maintain eye pressure. For example, a surgery previously requiring four ports may use not more than three ports. As another example, bimanual procedures may be performed using three incisions. Fewer incisions carry reduced risk of complications to the patient. Furthermore, the surgeon must monitor fewer incisions. Consequently, surgery may be made simpler, faster and less error prone. Because the optical fiber 110 is sufficiently thin for fluid to flow more freely in the channel 122, a high pressure for the infusion line may not be necessary. The optical fiber 110 is sufficiently robust to preclude or reduce damage from heat generated by the light carried in the optical fiber 110. Thus, the risk to the patient and ease of surgery are further improved.

Figure 2:
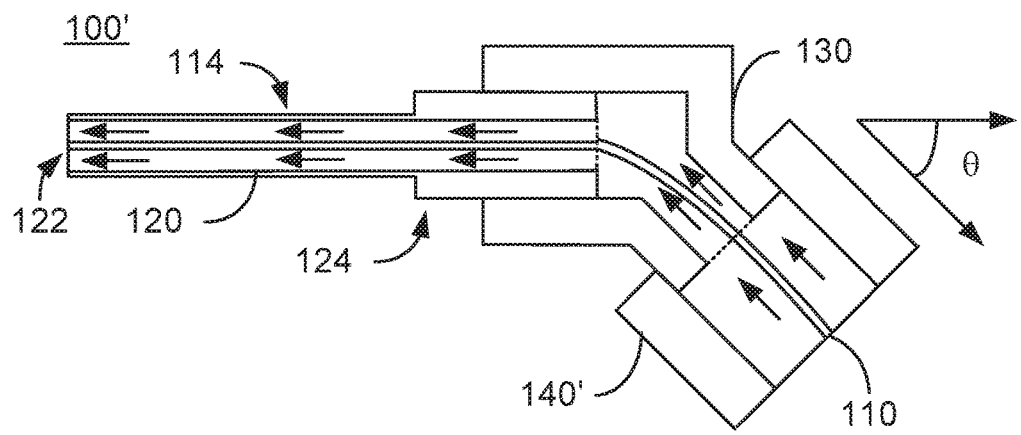
FIG. 2 depicts another exemplary embodiment of a surgical infusion device.

FIG. 2 depicts a side view of a portion of another exemplary embodiment of an illuminated infusion cannula 100' usable in ophthalmic surgery. FIG. 2 is not to scale and for explanatory purposes only. Thus, a particular illuminated infusion cannula is not intended to be shown. In addition, only some portions of the illuminated infusion cannula 100' are shown.

The illuminated infusion cannula 100' is analogous to the illuminated infusion cannula 100. Consequently, the illuminated infusion cannula 100' includes an optical fiber 110 and a cannula 120 that are analogous to the optical fiber 110 and cannula 120 of the illuminated infusion cannula 100. For example, the sizes and material(s) used for the cannula 120 and optical fiber 110 are analogous to those described above. Also shown in FIG. 2 is the infusion line 140' to which the illuminated infusion cannula 100' is connected.

The infusion line 140' is desired to be oriented at a nonzero angle, $\theta$, from the axis of channel 122. Thus, the fluid flow from the infusion line 140' is at the angle, $\theta$, from fluid flow through the cannula 120. This is in contrast to the situation shown in FIG. 1B, in which the direction of fluid flow through the infusion line 140 is substantially the same as that in the channel 122. In order to facilitate the change in direction of the fluid flow, an adapter 130 is added to the illuminated infusion cannula 100'. The adapter 130 may be connected with the cannula 120. In other embodiments, the cannula 120 and adapter 130 may be formed as a single piece. In either case, the direction of fluid flow may be altered.

The illuminated infusion cannula 100' may share the benefits of the illuminated infusion cannula 100. Because both illumination and fluid are provided via a single device 100', a single incision may be used to maintain eye pressure and provide light. For example, bimanual procedures previously requiring four ports may use not more than two ports. Fewer incisions carry reduced risk of complications to the patient and may make surgery simpler, faster and less error prone. Because the optical fiber 110 is sufficiently thin for fluid to flow more freely in the channel 122, a high pressure for the infusion line may not be necessary. The optical fiber 110 is sufficiently robust to preclude or reduce damage from heat generated by the light carried in the optical fiber 110. Thus, the risk to the patient and ease of surgery are further improved.

FIGS. 3A-3E depict side views of another exemplary embodiment of an illuminated infusion cannula 100" usable in ophthalmic surgery. The illuminated infusion cannula 100" is analogous to the illuminated infusion cannulas 100 and/or 110'. Consequently, the illuminated infusion cannula 100" includes an optical fiber 110 and a cannula 120' that are analogous to the optical fiber 110 and cannula 120 of the illuminated infusion cannula 100 and/or 100'. For example, the sizes and material(s) used for the cannula 120' and optical fiber 110 are analogous to those described above. Also shown in FIGS. 3A-3E is the infusion line 140" to which the illuminated infusion cannula 100' is connected.

Figure 3A:
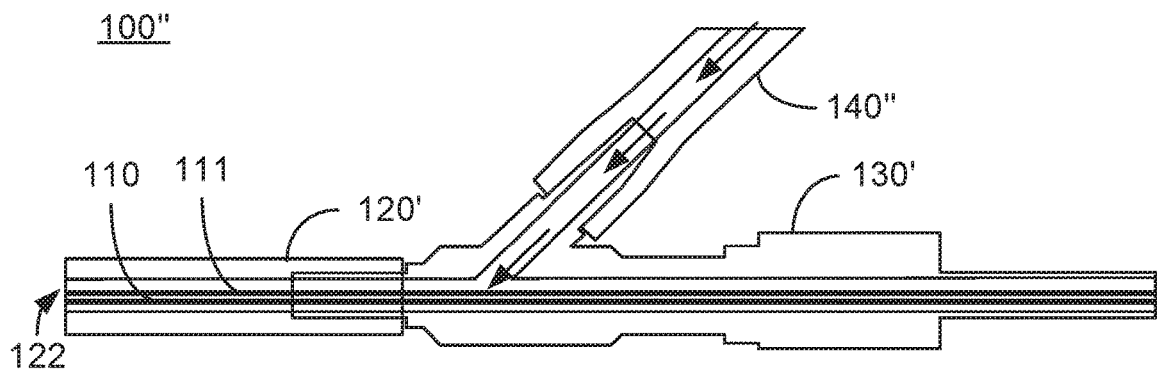
FIGS. 3A, 3B, 3C, 3D, and 3E depict portions of another exemplary embodiment of a surgical infusion device.
Figure 3B:
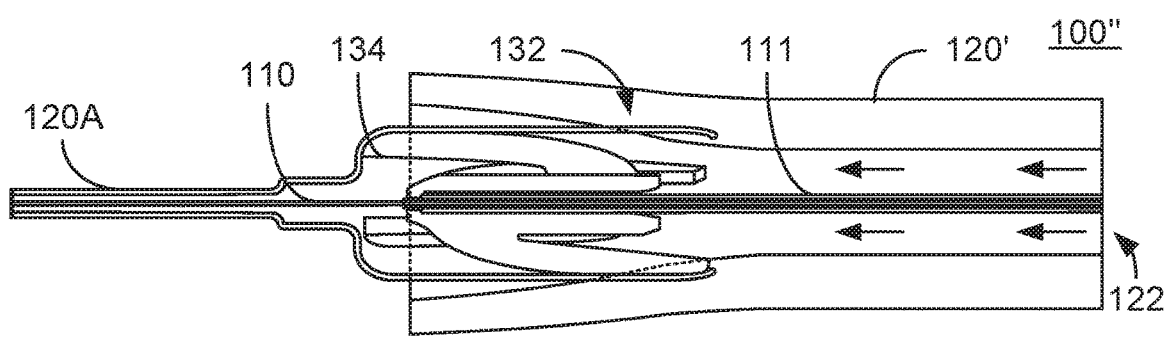
Figure 3C:
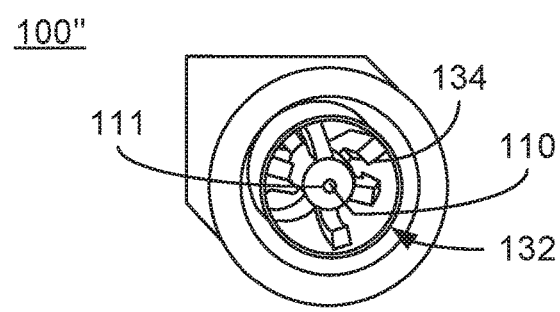

FIG. 3A depicts the illuminated infusion cannula 100" in the region where the fluid, such as BSS®, is added to a channel including the optical fiber. FIG. 3B depicts the distal region of the illuminated infusion cannula 100" where the optical fiber 110 exits the channel. FIG. 3C is a cross-sectional view of the distal end of the illuminated infusion cannula 100". FIGS. 3A-3E are not to scale and for explanatory purposes only. Thus, a particular illuminated infusion cannula is not intended to be shown. In addition, only some portions of the illuminated infusion cannula 100" are shown.

The illuminated infusion cannula 100" also includes an optical fiber tube 111, a Y-adapter 130' and a spider-shaped hub 134. The optical fiber tube 111 contains and protects the optical fiber 110. The Y-adapter 130' allows the fluid to be provided to the channel 122. The direction of travel of the fluid is shown in FIGS. 3A and 3B by arrows within the channel 122' and within the infusion line 140'. Also shown is nozzle 120A and spider 134. The nozzle 120A may be a 23 gauge, 25 gauge or 27 gauge cannula. The nozzle 120A contains the fiber outside of the remaining portion of the illuminated infusion cannula 100' and within the eye. The spider-shaped hub 134 has multiple opposed flexible members (e.g., arranged in a plurality of longitudinally disposed groups) to provide stable attachment of the fiber within a proximal portion of the cannula 100'. The spider aids in positioning the fiber tip at the proper location with respect to nozzle 120A to distribute the desired light pattern, and in allowing for coaxial flow without significantly restricting flow.

In some embodiments, as seen in FIGS. 3B-C, the spider shaped hub 134 may position the optical fiber 110 in the center of the cannula 100 (and, for example, in the center of the nozzle 120A). In some embodiments, the optical fiber 110 may start in a central portion at the proximal end of the cannula 100 (the end extending outside of the eye). The optical fiber 110 may then emerge from the spider shaped hub 134 into the central portion of the nozzle 120A. The optical fiber 110 may be rigid such that the optical fiber 110 tends to stay toward the center of the cannula 100 (and nozzle 120A) even as the optical fiber 110 extends toward the distal end of the nozzle 120A. Further, the optical fiber 110 may extend down cannula 100 (and down the nozzle 120A) off of an interior channel wall such that infusion fluid flowing down the nozzle 120A circumscribes the optical fiber 110. In some embodiments, fluid flow around the optical fiber 110 may further reinforce the optical fiber's position in the center (i.e., fluid flow may bias the optical fiber 110 toward the center of the nozzle 120A as the fluid flows down the nozzle 120A on all sides of the optical fiber 110).

The illuminated infusion cannula 100" may share the benefits of the illuminated infusion cannula 100 and/or 100'. Because both illumination and fluid are provided via a single device 100", a single incision may be used to maintain eye pressure and provide light. For example, bimanual procedures previously requiring four ports may use not more than two ports. Fewer incisions carry reduced risk of complications to the patient and may make surgery simpler, faster and less error prone. Because the optical fiber 110 is sufficiently thin for fluid to flow more freely in the channel 122, a high pressure for the infusion line may not be necessary. The optical fiber 110 is sufficiently robust to preclude or reduce damage from heat generated by the light carried in the optical fiber 110. Thus, the risk to the patient and ease of surgery are further improved.

FIG. 4A depicts a side view of another exemplary embodiment of an illuminated infusion cannula 150 usable in ophthalmic surgery. FIG. 4B is a cross-sectional view of a portion of the illuminated infusion cannula. FIGS. 4A-4B are not to scale and for explanatory purposes only. Thus, a particular illuminated infusion cannula is not intended to be shown. In addition, only some portions of the illuminated infusion cannula 150 are shown.

The illuminated infusion cannula 150 includes an optical fiber 160 and a cannula 170 that are analogous to the optical fiber 110 and cannula 120, respectively. The cannula 170 is hollow and has a channel 172 that is parallel to the axis and analogous to the channel 122. The inside diameter of the cannula 170, d1, is the diameter of the channel 172. The outside diameter of the cannula 170 is d2. In some embodiments, the inside diameter d1 is on the order of three hundred through five hundred micrometers. For example, the cannula 170 may be a 23, 25 or 27 gauge cannula. However, other sizes are possible.

The optical fiber 160 is analogous to the optical fiber 110 and may have similar diameters. Thus, the diameter, t, of the optical fiber 160 may not be more than one half of the diameter of the channel 172. In some embodiments, t may not be more than one third of d1. In some such embodiments, the optical fiber diameter may not be more than one hundred micrometers. In other embodiments, the diameter of the optical fiber 160 may not be more than sixty micrometers. The diameter of the optical fiber 160, t, may be not more than fifty micrometers. In some cases, t may be at least thirty micrometers. The diameter of the optical fiber 160 is such that the optical fiber 160 can transmit the desired amount of light without heat induced damage while being sufficiently small to allow fluid to flow through the channel 172. As can be seen in FIGS. 3A-3B, the optical fiber 160 may be along the axis (center) of the channel 172. However, other locations may be possible. In some embodiments, the optical fiber 160 may be secured to a central portion at the proximal end of the cannula 170 (the end extending out of the eye). For example, the optical fiber 160 may emerge from spider shaped hub 134 (e.g., secured to a proximal end of the cannula 170) in a central portion of the needle 170. The optical fiber 160 may be rigid such that the optical fiber 160 tends to stay in central position of the channel 172 even as the optical fiber 160 extends toward the distal end of the nozzle 120A. Further, the optical fiber 160 may extend down the channel 172 off of an interior channel wall such that infusion fluid flowing down the channel 172 circumscribes the optical fiber 160. A portion 162 of the optical fiber 160 protrudes from the cannula 150. In other embodiments, the optical fiber 160 may terminate at the tip of or within the channel 172. Although a flat cleaved tip is shown for the optical fiber 160, other tips may be used.

The illuminated infusion cannula 150 shares the benefits of the illuminated infusion cannula 100. Both illumination and fluid are provided via a single device 150. Thus, light may be provided and eye pressure maintained using only a single incision in the eye. Fewer incisions carry reduced risk of complications to the patient. Furthermore, surgery may be made simpler, faster and less error prone. Because the optical fiber 160 is sufficiently thin, the optical fiber 160 occupies a small fraction of the cross-sectional area of the channel 172. Thus, fluid may flow more freely in the channel 172 and a high pressure for the infusion line may not be necessary. The optical fiber 160 is sufficiently robust to preclude or reduce damage from heat generated by the light carried in the optical fiber 160. Thus, the risk to the patient and ease of surgery are further improved.

FIG. 5A depicts a side view of another exemplary embodiment of an illuminated infusion cannula 150A usable in ophthalmic surgery. FIG. 5B is a cross-sectional view of a portion of the illuminated infusion cannula 150A. FIGS. 5A-5B are not to scale and for explanatory purposes only. Thus, a particular illuminated infusion cannula is not intended to be shown. In addition, only some portions of the illuminated infusion cannula 150A are shown.

The illuminated infusion cannula 150A includes an optical fiber 160' and a cannula 170 that are analogous to the optical fiber 160 and cannula 170, respectively. The cannula 170 is hollow and has a channel 172. The inside diameter of the cannula 170, d1, is the diameter of the channel 172. The outside diameter of the cannula 170 is d2.

Figure 3D:
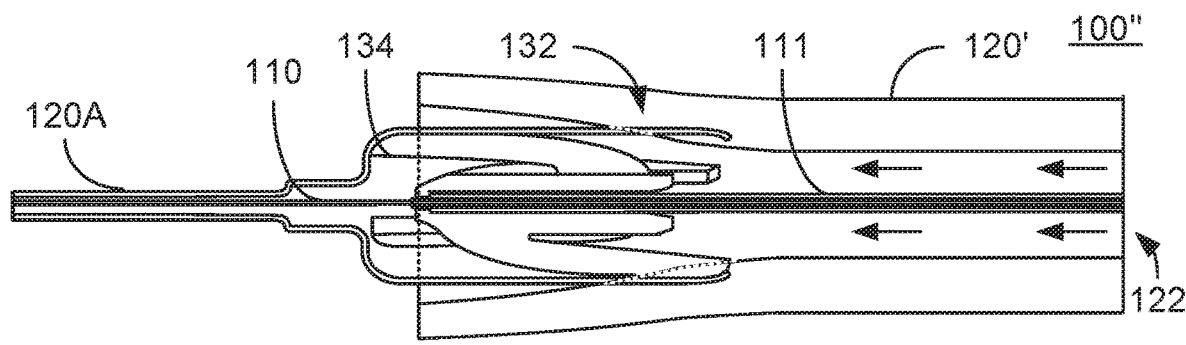
Figure 3E:
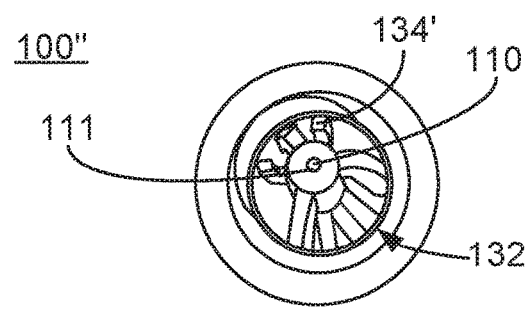

The optical fiber 160' is analogous to the optical fiber 160 and may have similar diameters. Thus, t, d1 and d2 may be analogous to those described above. However, the optical fiber 160' terminates at the end of the channel 172. In addition, the optical fiber 160' is shown as residing off of the axis for the channel 172. Thus, there is no requirement that an optical fiber lie along the axis, against a wall of the channel 172 or at a particular location. In some embodiments, as seen in FIGS. 3D-E, the optical fiber 160' may be secured to an off-axis portion at the proximal end of the cannula 170 (the end extending out of the eye). For example, the optical fiber 160' may emerge from an eccentrically shaped spider shaped hub 134' (which functions similar to spider shaped hub 134, but with legs configured to place the optical fiber 160' in an off-axis portion of the channel 172). The optical fiber 160' may be rigid such that the optical fiber 160' tends to stay in the off-axis position of the channel 172 even as the optical fiber 160' extends toward the distal end of the nozzle 120A. Further, the optical fiber 160' may extend down the channel 172 off of an interior channel wall such that infusion fluid flowing down the channel 172 circumscribes the optical fiber 160'. Although a flat cleaved tip is shown for the optical fiber 160', other tips may be used.

The illuminated infusion cannula 150A shares the benefits of the illuminated infusion cannula 150. Both illumination and fluid are provided via a single device 150A. Thus, only one incision may be made in the eye to provide light and maintain eye pressure. Fewer incisions carry reduced risk of complications to the patient and may make surgery simpler, faster and less error prone. Because the optical fiber 160 is sufficiently thin for fluid to flow more freely in the channel 172, a high pressure for the infusion line may not be necessary. The optical fiber 160' is sufficiently robust to preclude or reduce damage from heat generated by the light carried in the optical fiber 160'. Thus, the risk to the patient and ease of surgery are further improved.

FIG. 6A depicts a side view of another exemplary embodiment of an illuminated infusion cannula 150B usable in ophthalmic surgery. FIG. 6B is a cross-sectional view of a portion of the illuminated infusion cannula 150B. FIGS. 6A-6B are not to scale and for explanatory purposes only. Thus, a particular illuminated infusion cannula is not intended to be shown. In addition, only some portions of the infusing illuminated infusion cannula 150B are shown.

The illuminated infusion cannula 150B includes an optical fiber 160" and a cannula 170' that are analogous to the optical fiber 160 and/or 160' and cannula 180, respectively. The cannula 170' is hollow and has a channel 172'. The inside diameter of the cannula 170', d1, is the diameter of the channel 172'. The outside diameter of the cannula 170' is d2. In addition, the channel 172' includes a depression 174, or groove, in which the optical fiber 160" resides. The groove 174 may be used to guide and retain the optical fiber 160" in the channel 172'. In some embodiments, epoxy, resin or another substance may be used to hold the optical fiber 160" in the groove 174. The epoxy may also serve to provide mechanical protection, optical isolation, heat sinking, or serve another purpose for the optical fiber 160".

The optical fiber 160" is analogous to the optical fibers 160 and/or 160' and may have similar diameters. Thus, t, d1 and d2 may be analogous to those described above. The optical fiber 160" may terminate outside of the channel 172' as shown or at another location. In addition, the optical fiber 160" is shown as residing at a particular location along the wall of the chamber 172. Other locations are possible. Although a flat cleaved tip is shown for the optical fiber 160", other tips may be used The illuminated infusion cannula 150B shares the benefits of the illuminated infusion cannula 150 and/or 150A. Both illumination and fluid are provided via a single device 150B. Consequently, a single incision in the eye may be used both to provide light and maintain eye pressure. Fewer incisions carry reduced risk of complications to the patient. Surgery may also be simpler, faster and less error prone. Because the optical fiber 160" occupies a small area of the cross section of the channel 172', fluid may flow more freely in the channel 172. A high pressure for the infusion line may not be necessary. The optical fiber 160" is sufficiently robust to preclude or reduce damage from heat generated by the light carried in the optical fiber 160". Use of epoxy or an analogous substance may also improve the robustness of the optical fiber 160". Thus, the risk to the patient and ease of surgery are further improved.

FIG. 7A depicts a side view of another exemplary embodiment of an illuminated infusion cannula 150C usable in ophthalmic surgery. FIG. 7B is a cross-sectional view of a portion of the illuminated infusion cannula 150C. FIGS. 7A-7B are not to scale and for explanatory purposes only. Thus, a particular illuminated infusion cannula is not intended to be shown. In addition, only some portions of the illuminated infusion cannula 150C are shown.

The illuminated infusion cannula 150C includes an optical fiber 160''' and a cannula 170" that are analogous to the optical fiber 160 and/or 160' and cannula 170 and/or 170', respectively. The cannula 170" is hollow and has a channel 172'. The inside diameter of the cannula 170", d1, is the diameter of the channel 172". The outside diameter of the cannula 170" is d2. In addition, the channel 172" includes a depression 174', or groove, in which the optical fiber 160''' resides. In this case, the groove 174 may not be parallel to the axis of the channel 172". In some embodiments, epoxy, resin or another substance may be used to hold the optical fiber 160''' in the groove 174'. The epoxy may also serve to provide mechanical protection, optical isolation, heat sinking or serve another purpose for the optical fiber 160'''.

The optical fiber 160''' is analogous to the optical fibers 160/160' and may have similar diameters. Thus, t, d1 and d2 may be analogous to those described above. The optical fiber 160''' may terminate inside of the channel 172" as shown or at another location. In addition, the optical fiber 160''' is shown as residing at a particular location along the wall of the chamber 172. Other locations are possible. Although a flat cleaved tip is shown for the optical fiber 160''', other tips may be used.

The illuminated infusion cannula 150C shares the benefits of the illuminated infusion cannula 150, 150A and/or 150B. Because both illumination and fluid are provided via a single device 150C, only one incision may be made in the eye to provide light and maintain eye pressure. Fewer incisions carry reduced risk of complications to the patient and may make surgery simpler, faster and less error prone. Because the optical fiber 160''' is sufficiently thin for fluid to flow more freely in the channel 172", a high pressure for the infusion line may not be necessary. The optical fiber 160''' is sufficiently robust to preclude or reduce damage from heat generated by the light carried in the optical fiber 160'''. Use of epoxy or an analogous substance may also improve the robustness of the optical fiber 160'''. Thus, the risk to the patient and ease of surgery are further improved.

FIG. 8A depicts a side view of another exemplary embodiment of an illuminated infusion cannula 150D usable in ophthalmic surgery. FIG. 8B is a cross-sectional view of a portion of the illuminated infusion cannula 150D. FIGS. 8A-8B are not to scale and for explanatory purposes only.

Thus, a particular illuminated infusion cannula is not intended to be shown. In addition, only some portions of the illuminated infusion cannula 150D are shown.

The illuminated infusion cannula 150D includes an optical fiber 160'''' and a cannula 170''' that are analogous to the optical fiber 160, 160', 160", and/or 160''' and cannula 170, 170' and/or 170'', respectively. The cannula 170''' is hollow and has a channel 172'''. The inside diameter of the cannula 170''', d1, is the diameter of the channel 172'''. The outside diameter of the cannula 170''' is d2. In addition, the outside of the cannula 170''' includes a depression 174'', or groove, in which the optical fiber 160'''' resides. In this case, the groove 174'' is parallel to the axis of the channel 172''. However, another configuration is possible. In some embodiments, epoxy, resin or another substance may be used to hold the optical fiber 160'''' in the groove 174''. The epoxy may also serve to provide mechanical protection, optical isolation, heat sinking or serve another purpose for the optical fiber 160''''. Because the optical fiber 160' is outside of the channel 172''', more space in the channel is available for fluid flow.

The optical fiber 160'''' is analogous to the optical fibers 160, 160', 160" and/or 160''' and may have similar diameters. Thus, t, d1 and d2 may be analogous to those described above. The optical fiber 160'''' may terminate at the end of the channel 172''' as shown or at another location. In addition, the optical fiber 160'''' is shown as residing at a particular location along the wall of the chamber 172. Other locations are possible. Although a flat cleaved tip is shown for the optical fiber 160'''' other tips may be used The illuminated infusion cannula 150D shares the benefits of the illuminated infusion cannula 150, 150A, 150B and/or 150C. Both illumination and fluid are provided via a single device 150D. Thus, only one incision may be made in the eye to provide light and maintain eye pressure. Fewer incisions carry reduced risk of complications to the patient, may make surgery simpler and faster and less error prone. Because the optical fiber 160'''' is outside of the channel 172''' fluid may flow more freely in the channel 172''. Thus, a high pressure for the infusion line may not be necessary. The optical fiber 160'''' is sufficiently robust to preclude or reduce damage from heat generated by the light carried in the optical fiber 160''''. Use of epoxy or an analogous substance may also improve the robustness of the optical fiber 160''''. Thus, the risk to the patient and ease of surgery are further improved.

FIG. 9 depicts a side view of another exemplary embodiment of an optical fiber 190 that may be used in an illuminated infusion cannula usable in ophthalmic surgery. FIG. 9 is not to scale and for explanatory purposes only. Thus, a particular optical fiber is not intended to be shown. In addition, only some portions of the optical fiber 190 are shown. The optical fiber 190 may be used in an illuminated infusion cannula 100, 100', 150, 150A, 150B, 150C, 150D and/or another illuminated infusion cannula. Also shown are input beam 191 and output light 193.

The optical fiber 190 is analogous to the optical fibers 110, 160, 160', 160", 160''', and/or 160'''' and may have similar diameters. The diameter of the optical fiber 190 is t. Thus, t may be analogous to that described above. In addition, the optical fiber 190 has a tip 192. The tip 192 is tapered. As a result, the output light 193 may be more efficiently spread. Thus, light may illuminate a larger region.

The optical fiber 190 shares the benefits of the optical fiber 110, 160, 160', 160", 160''' and/or 160'''' when used in an illuminated infusion cannula. Both illumination and fluid may be provided via a single device. Fewer incisions may be made and surgery may be simpler and faster. The optical fiber 190 may also be formed of silica or like materials to ensure they remain robust despite rises in temperature due to light carried in the fiber 190. The optical fiber 190 is sufficiently robust to preclude or reduce damage from heat generated by the light carried in the optical fiber 190. Thus, the risk to the patient and ease of surgery are further improved.

FIG. 10 depicts a side view of another exemplary embodiment of an optical fiber 190' that may be used in an illuminated infusion cannula usable in ophthalmic surgery. FIG. 10 is not to scale and for explanatory purposes only. Thus, a particular optical fiber is not intended to be shown. In addition, only some portions of the optical fiber 190' are shown. The optical fiber 190' may be used in an illuminated infusion cannula 100, 100', 150, 150A, 150B, 150C, 150D and/or another illuminated infusion cannula. Also shown are input beam 191 and output light 193.

The optical fiber 190' is analogous to the optical fibers 110, 160, 160', 160", 160''', 160'''' and/or 190 and may have similar diameters. The diameter of the optical fiber 190' is d. Thus, t may be analogous to that described above. In addition, the optical fiber 190 has a tip 192'. The tip 192' may more efficiently scatter light. Although an ellipsoid is shown for the tip 192', the scattering tip 192' may have another shape that scatters light. Thus, the output light 193 may illuminate a larger region.

The optical fiber 190' shares the benefits of the optical fiber 110, 160, 160', 160", 160''', 160'''' and/or 190 when used in an illuminated infusion cannula. Both illumination and fluid may be provided via a single device. Fewer incisions may be made and surgery may be simpler and faster. The optical fiber 190' may also be formed of silica or like materials to ensure they remain robust despite rises in temperature due to light carried in the fiber 190'. The optical fiber 190' is sufficiently robust to preclude or reduce damage from heat generated by the light carried in the optical fiber 190'. Thus, the risk to the patient and ease of surgery are further improved.

Figure 11:
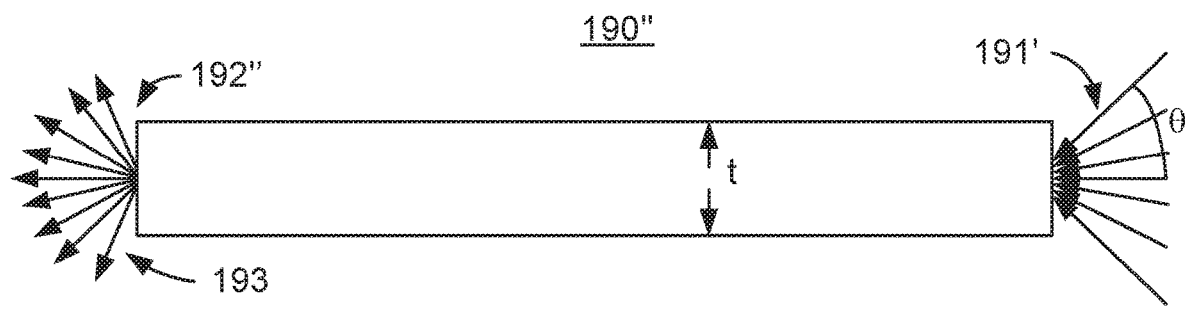
FIG. 11 depicts another exemplary embodiment of an optical fiber usable in an illuminated infusion cannula.

FIG. 11 depicts a side view of another exemplary embodiment of an optical fiber 190' that may be used in an illuminated infusion cannula usable in ophthalmic surgery. FIG. 11 is not to scale and for explanatory purposes only. Thus, a particular optical fiber is not intended to be shown. In addition, only some portions of the optical fiber 190'' are shown. The optical fiber 190'' may be used in an illuminated infusion cannula 100, 100', 150, 150A, 150B, 150C, 150D and/or another illuminated infusion cannula. Also shown are input beam 191' and output light 193.

The optical fiber 190'' is analogous to the optical fibers 110, 160, 160', 160", 160''', 160'''', 190 and/or 190' and may have similar diameters. The diameter of the optical fiber 190'' is d. Thus, t may be analogous to that described above. In addition, the optical fiber 190 has a flat cleaved tip 192''. In order for the tip 192'' to more efficiently spread light, the input light 191' may be at a higher angle, $\theta$. For example, $\theta$ may be at least thirty degrees and less than ninety degrees. The numerical aperture for the fiber 190'' may also be correspondingly large to accept the large angle of the input light 191'. Thus, the output light 193 may illuminate a larger region. In an alternate embodiment, the optical fiber 190'' might be tapered in the middle to increase the angular content of light before reaching to the flat cleaved tip 192''. In such an embodiment, the input angle of the light may be less than thirty degrees.

The optical fiber 190'' shares the benefits of the optical fiber 110, 160, 160', 160", 160''', 160'''', 190 and/or 190' when used in an illuminated infusion cannula. Both illumination and fluid may be provided via a single device. Fewer incisions may be made and surgery may be simpler and faster. The optical fiber 190" may also be formed of silica or like materials to ensure they remain robust despite rises in temperature due to light carried in the fiber 190". The optical fiber 190" is sufficiently robust to preclude or reduce damage from heat generated by the light carried in the optical fiber 190". Thus, the risk to the patient and ease of surgery are further improved.

Various characteristics of illuminated infusion cannulas and optical fibers have been shown. One of ordinary skill in the art will recognize that one or more of these features may be combined in manners not explicitly shown herein.

Figure 12:
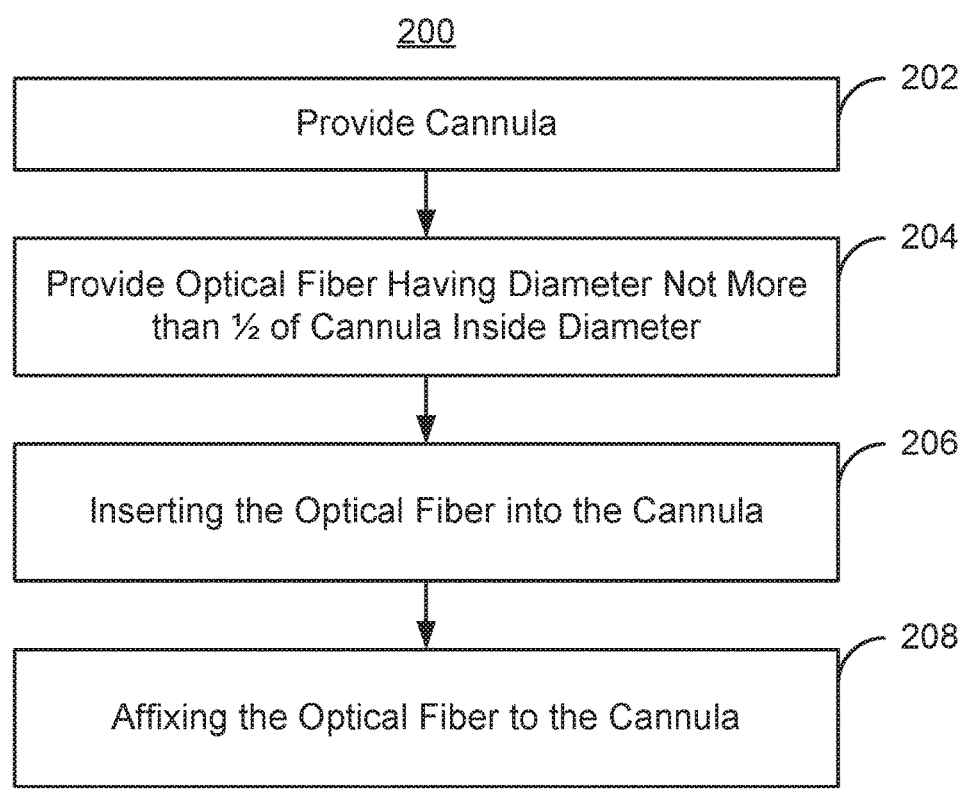
FIG. 12 is a flow chart depicting an exemplary embodiment of a method for providing an illuminated infusion cannula.

FIG. 12 is a flow chart of an exemplary embodiment of a method 200 for providing an illuminated infusion cannula such as the illuminated infusion cannula(s) 100, 100', 150, 150A, 150B, 150C and/or 150D. For simplicity, some elements may be omitted, interleaved, and/or combined. The method 200 is also described in the context of the illuminated infusion cannula 100. However, the method 200 may be used to form the illuminated infusion cannula 100', 150, 150A, 150B, 150C, 150D and/or an analogous illuminated infusion cannulas.

The cannula 120 is provided, via 202. The optical fiber 110 is also provided, via 204. Element 206 may include inserting the optical fiber 110 into the cannula (e.g., into the channel 122), and element 208 may include affixing the optical fiber to the cannula (e.g, through an adhesive applied between the optical fiber 110 and the channel 122). Using the method 200, the illuminated infusion cannula 100, 100', 150, 150A, 150B, 150C and/or 150D may be fabricated. Thus, the benefits of one or more of the illuminated infusion cannula 100, 100', 150, 150A, 150B, 150C and/or 150D may be achieved.

Figure 13:
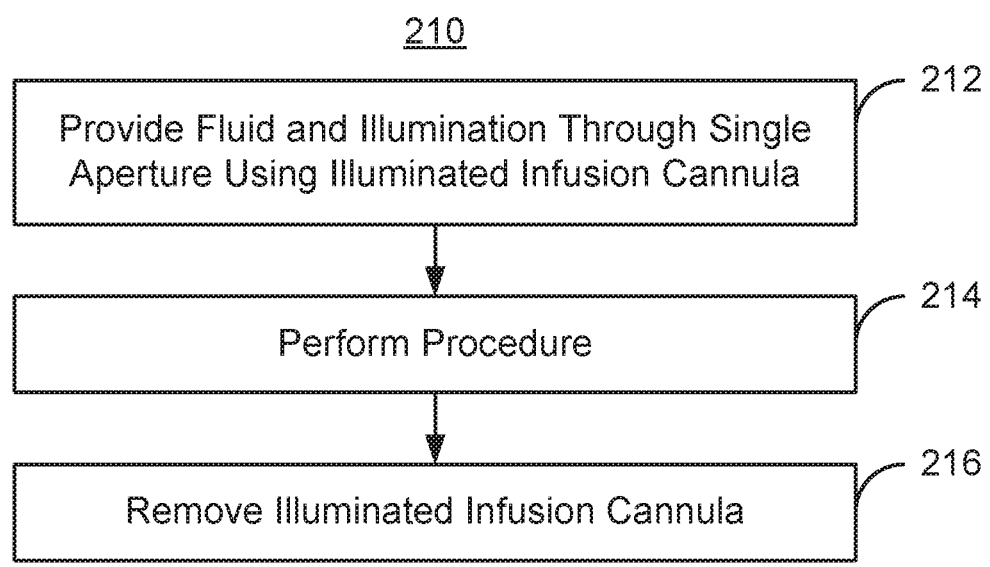
FIG. 13 is a flow chart depicting an exemplary embodiment of a method for assisting a physician using an illuminated infusion cannula.

FIG. 13 is a flow chart depicting an exemplary embodiment of a method 210 for assisting a physician during ophthalmic surgery using an illuminated infusion cannula such as the illuminated infusion cannula 100, 100', 150, 150A, 150B, 150C and/or 150D. For simplicity, some elements may be omitted, interleaved, performed in another order and/or combined. The method 210 is described in the context of ophthalmic surgery and the illuminated infusion cannula 100. However, the method 210 may be extended to other types of surgery.

The method may commence after surgery has started. Fluid such as BSS® and illumination are provided via the illuminated infusion cannula 100, via 212. Thus, element 212 may include the surgeon making an incision in the eye of the patient and performing other required tasks. The surgeon may also insert the cannula 120 into the incision in patient's eye at 212. Alternatively, the surgeon may insert the cannula 120 into another cannula, such as a trocar cannula, that is inserted into the eye. The fluid and illumination may be provided through the illuminated infusion cannula 100 within the trocar cannula. Thus, the pressure of the eye may be maintained and the operating field illuminated.

The desired procedure is performed, via 214. Thus, portions of the vitreous may be removed. Other procedures may also be performed. The cannula 120 may then be removed, via 216

Using the method 210 and the illuminated infusion cannula 100, 100', 150, 150A, 150B, 150C and/or 150D, ophthalmic surgery may be facilitated and patient safety may be improved. A method and system for providing an illuminated infusion cannula, particularly for ophthalmic surgery, have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. A surgical infusion device, comprising:
a cannula having a channel therethrough, the channel having an inside diameter, the cannula having an outside diameter greater than the inside diameter; and
an optical fiber coupled with the cannula, wherein the optical fiber is coupled with the cannula and wherein the optical fiber has an optical fiber diameter of at least thirty micrometers and less than one hundred micrometers;
wherein at least a portion of the optical fiber coupled with the cannula is within the channel;
wherein the at least the portion of the optical fiber within the channel is in contact with infusion fluid flowing through the cannula;
wherein the device further comprises a hub, the optical fiber is positioned in the channel by the hub, the hub further including a plurality of members extending substantially radially from the hub and contacting an inside surface of the cannula.

2. The surgical infusion device of claim 1, wherein the optical fiber has a diameter of not more than one half the inside diameter of the channel.

3. The surgical infusion device of claim 2, wherein the optical fiber diameter is not more than fifty micrometers.

4. The surgical infusion device of claim 1, wherein the plurality of members are flexible.

5. The surgical infusion device of claim 1, wherein the plurality of members are arranged in a plurality of longitudinally disposed groups.

6. The surgical infusion device of claim 1, wherein the cannula is connectable to an infusion line such that fluid may be provided through the channel.

7. The surgical infusion device of claim 6, wherein the channel has a first axis and the infusion line has a second axis corresponding to a direction of fluid flow from the infusion line, the surgical infusion device further comprising:
an adapter coupled with the cannula such that the infusion line is connectable to the cannula at a nonzero connection angle, the nonzero connection angle being an angle between the first axis and the second axis.

8. The surgical infusion device of claim 1, wherein the cannula includes an end and the optical fiber includes a tip proximate to the end of the cannula.

9. The surgical infusion device of claim 8, wherein the tip is selected from a tapered tip, a scattering tip and a flat cleaved tip.

10. The surgical infusion device of claim 1, wherein the cannula includes a surface having a depression therein, with the at least the portion of the optical fiber resides in the depression.

11. The surgical infusion device of claim 10, wherein the depression adjoins the channel.

12. The surgical infusion device of claim 8, wherein the tip is a flat cleaved tip and a corresponding input beam has a launch half-angle of at least thirty degrees.

13. A surgical infusion device, comprising:
a cannula having an end and having a channel therethrough, the channel having an inside diameter, the cannula having an outside diameter greater than the inside diameter;
an optical fiber coupled with the cannula and having a tip, at least a portion of the optical fiber residing in the channel and having a diameter of at least thirty micrometers and not more than fifty micrometers, the tip being selected from a tapered tip, a scattering tip and a flat cleaved tip; and
an infusion line coupled with the channel such that fluid may be provided through the channel and adjacent to the at least the portion of the optical fiber;
a hub, the optical fiber being positioned in the channel by the hub, the hub further including a plurality of members extending substantially radially from the hub and contacting an inside surface of the cannula;
wherein the plurality of members are flexible and arranged in a plurality of longitudinally disposed groups.

* * * * *